US011701007B2

(12) United States Patent
Hanson et al.

(10) Patent No.: US 11,701,007 B2
(45) Date of Patent: Jul. 18, 2023

(54) SYSTEMS AND METHODS FOR BIOMETRIC TAMPER DETECTION

(71) Applicant: BI Incorporated, Boulder, CO (US)

(72) Inventors: Duke Hanson, Boulder, CO (US);
Joseph P. Newell, Boulder, CO (US);
Dustin Pettit, Boulder, CO (US);
Evencio Fernandez, Boulder, CO (US);
Ric Miller, Boulder, CO (US)

(73) Assignee: BI Incorporated, Boulder, CO (US)

( * ) Notice: Subject to any disclaimer, the term of this patent is extended or adjusted under 35 U.S.C. 154(b) by 378 days.

(21) Appl. No.: 17/006,753

(22) Filed: Aug. 28, 2020

(65) Prior Publication Data

US 2022/0061680 A1    Mar. 3, 2022

(51) Int. Cl.
| | |
|---|---|
| *A61B 5/0205* | (2006.01) |
| *A61B 5/00* | (2006.01) |
| *A61B 5/11* | (2006.01) |
| *A61B 5/145* | (2006.01) |
| *A61B 5/1172* | (2016.01) |
| *A61B 5/1171* | (2016.01) |
| *A61B 5/25* | (2021.01) |

(Continued)

(52) U.S. Cl.
CPC ........ *A61B 5/02055* (2013.01); *A61B 5/0022* (2013.01); *A61B 5/0077* (2013.01); *A61B 5/11* (2013.01); *A61B 5/1172* (2013.01); *A61B 5/1176* (2013.01); *A61B 5/14542* (2013.01); *A61B 5/25* (2021.01); *A61B 5/681* (2013.01); *A61B 5/742* (2013.01); *A61B 5/7405* (2013.01); *A61B 5/7455* (2013.01); *G06Q 50/265* (2013.01); *G08B 21/22* (2013.01); *G08B 29/046* (2013.01); *H04W 12/06* (2013.01); *A61B 5/02438* (2013.01)

(58) Field of Classification Search
CPC . A61B 5/02055; A61B 5/0022; A61B 5/0077; A61B 5/11; A61B 5/1172; A61B 5/1176; A61B 5/14542; A61B 5/25; A61B 5/681; A61B 5/7405; A61B 5/742; A61B 5/7455; A61B 5/02438; A61B 5/318; A61B 2562/0257; A61B 5/1112; G06Q 50/265; G08B 21/22; G08B 29/046; G08B 21/0211; G08B 7/06; G08B 21/0269; H04W 12/06; G06V 40/40
See application file for complete search history.

(56) References Cited

U.S. PATENT DOCUMENTS

| | | |
|---|---|---|
| 4,475,481 A | 10/1984 | Carrol |
| 4,549,264 A | 10/1985 | Carrol |

(Continued)

FOREIGN PATENT DOCUMENTS

| | | |
|---|---|---|
| WO | WO/1998/008204 | 2/1998 |
| WO | WO/2000/077688 | 12/2000 |

(Continued)

OTHER PUBLICATIONS

U.S. Appl. No. 12/041,746, filed Mar. 4, 2008, Buck, et al.

(Continued)

*Primary Examiner* — Omeed Alizada
(74) *Attorney, Agent, or Firm* — HDC Intellectual Property Law, LLP

(57) ABSTRACT

Various embodiments provide systems and methods for detecting tampering with a monitoring device using biometric data.

25 Claims, 9 Drawing Sheets

(51) Int. Cl.
*G06Q 50/26* (2012.01)
*G08B 21/22* (2006.01)
*G08B 29/04* (2006.01)
*H04W 12/06* (2021.01)
*A61B 5/024* (2006.01)

(56) References Cited

U.S. PATENT DOCUMENTS

| | | | |
|---|---|---|---|
| 4,658,357 A | 4/1987 | Carrol | |
| 4,724,427 A | 2/1988 | Carrol | |
| 4,777,477 A | 10/1988 | Watson | |
| 4,821,823 A | 4/1989 | Skibinski | |
| 4,843,377 A | 6/1989 | Fuller | |
| 4,857,893 A | 8/1989 | Carrol | |
| 4,885,571 A | 12/1989 | Pauley | |
| 4,916,435 A | 4/1990 | Fuller | |
| 4,918,432 A | 4/1990 | Pauley | |
| 4,996,161 A | 2/1991 | Conners | |
| 4,999,613 A | 3/1991 | Williamson | |
| 5,043,736 A | 8/1991 | Damess | |
| 5,146,207 A | 9/1992 | Henry | |
| 5,220,919 A | 6/1993 | Phillips et al. | |
| 5,627,520 A | 5/1997 | Grubbs et al. | |
| 5,731,757 A | 3/1998 | Layson, Jr. | |
| 5,867,103 A | 2/1999 | Taylor, Jr. | |
| 5,889,474 A | 3/1999 | Ladue | |
| 5,923,300 A | 7/1999 | Meija | |
| 5,936,529 A | 8/1999 | Reisman et al. | |
| 5,939,529 A | 8/1999 | Reisman et al. | |
| 5,959,533 A | 9/1999 | Layson, Jr. | |
| 5,982,281 A | 11/1999 | Layson, Jr. | |
| 6,014,080 A | 1/2000 | Layson, Jr. | |
| 6,072,396 A | 6/2000 | Gaukel | |
| 6,130,620 A | 10/2000 | Pinnow et al. | |
| 6,160,481 A | 12/2000 | Taylor | |
| 6,218,945 B1 | 4/2001 | Taylor | |
| 6,512,456 B1 | 1/2003 | Taylor | |
| 6,606,304 B1 | 8/2003 | Grinter | |
| 6,674,368 B2 | 1/2004 | Hawkins et al. | |
| 6,700,547 B2 | 3/2004 | Mieja et al. | |
| 6,703,936 B2 | 3/2004 | Aninye | |
| 6,774,797 B2 | 8/2004 | Freathy | |
| 6,774,799 B2 | 8/2004 | Defant | |
| RE38,838 E | 10/2005 | Taylor | |
| 6,992,582 B2 | 1/2006 | Hill et al. | |
| 7,038,590 B2 | 5/2006 | Hoffman et al. | |
| 7,102,510 B2 | 9/2006 | Boling | |
| 7,119,695 B2 | 10/2006 | Defant | |
| 7,123,141 B2 | 10/2006 | Consestabile | |
| 7,205,890 B2 | 4/2007 | Defant | |
| RE39,909 E | 11/2007 | Taylor | |
| 7,330,122 B2 | 2/2008 | Derrick | |
| 7,386,152 B2 | 6/2008 | Rowe et al. | |
| 7,518,500 B2 | 4/2009 | Aninye | |
| 7,545,318 B2 | 6/2009 | Derrick | |
| 7,619,513 B2 | 11/2009 | Hill et al. | |
| 7,701,171 B2 | 4/2010 | Defant | |
| 7,737,841 B2 | 6/2010 | Derrick | |
| 7,804,412 B2 | 9/2010 | Derrick | |
| 7,930,927 B2 | 4/2011 | Cooper et al. | |
| 7,936,262 B2 | 5/2011 | Derrick | |
| 7,961,092 B2 | 6/2011 | Freathy et al. | |
| RE42,617 E | 9/2011 | Taylor | |
| 2002/0089434 A1* | 7/2002 | Ghazarian | G08B 13/06 |
| | | | 340/988 |
| 2002/0140559 A1 | 10/2002 | Zhou et al. | |
| 2003/0010998 A1 | 1/2003 | Callaway, Jr. | |
| 2003/0210149 A1 | 11/2003 | Reisman et al. | |
| 2004/0229560 A1* | 11/2004 | Maloney | G07C 9/28 |
| | | | 455/3.01 |
| 2004/0236199 A1 | 11/2004 | Hawthorne et al. | |
| 2005/0250440 A1 | 11/2005 | Zhou et al. | |
| 2006/0202836 A1 | 9/2006 | Hawthorne et al. | |
| 2006/0202837 A1 | 9/2006 | Hawthorne et al. | |
| 2008/0012760 A1 | 1/2008 | Derrick | |
| 2008/0108370 A1 | 5/2008 | Aninye | |
| 2008/0316022 A1 | 12/2008 | Buck et al. | |
| 2010/0240969 A1 | 3/2010 | Rompa | |
| 2010/0123589 A1 | 5/2010 | Buck et al. | |
| 2011/0154887 A1 | 3/2011 | Cooper et al. | |
| 2011/0133928 A1 | 6/2011 | Buck et al. | |
| 2011/0133937 A1 | 6/2011 | Buck et al. | |
| 2016/0004953 A1* | 1/2016 | Karani | G06K 19/07758 |
| | | | 235/492 |

FOREIGN PATENT DOCUMENTS

| | | |
|---|---|---|
| WO | WO/2005/019977 | 3/2005 |
| WO | WO/2005/038590 | 4/2005 |
| WO | WO/2006/108077 | 10/2006 |
| WO | WO/2006/121930 | 11/2006 |
| WO | WO/2006/122004 | 11/2006 |
| WO | WO/2007/027943 | 3/2007 |
| WO | WO/2007/037794 | 4/2007 |
| WO | WO/2008/008666 | 1/2008 |
| WO | WO/2008/008667 | 1/2008 |
| WO | WO/2008/008669 | 1/2008 |
| WO | WO/2008/008670 | 1/2008 |
| WO | WO/2008/027948 | 3/2008 |
| WO | WO/2008/027985 | 3/2008 |

OTHER PUBLICATIONS

U.S. Appl. No. 12/714,581, filed Mar. 1, 2010, Buck et al.

Marques, et al. "Evaluation of Transdermal Alcohol Devices" Pacific Institiute for Research and Evaluation, NHTSA Task Order DTNH22-02-D95121, pp. 1-31.

Marques, et al. "EvaluatingTransdermal Alcohol Measuring Devices" Pacific Institiute for Research and Evaluation, NHTSA, Nov. 2007 pp. 1-96.

Pollard et al. "Review of Technology to Prevent Alcohol-Impaired Crashes" U>S> Department of Transportation NHTSA, DOT HS 810 833, Sep. 2007, pp. 1-108.

Pollard, et al. "Vehilcle Technologies to Prevent Crashes Involving Alcohol-Impaired Drivers" The Volpe Center, Aug. 11, 2006, pp. 1-28.

Ratcliffe, "www.stltoday.com," Dec. 26, 2007, pp. 1-2. Retrieved from internet http://www.stltoday.com/stltoday/emaf.nsf/Popup retrieved on Jan. 18, 2008.

Roberson, et al. "Continuous Transdermal Alcohol Monitoring : A primer for Criminal Justice Professionals" Traffic Injury Research Foundation, Oct. 2006, pp. 1-34.

Shellem, "SCRAM Can Alert Probation Officers if Someone's Been Drinking", The Patriot-News, Nov. 25, 2007, pp. 1-3.

* cited by examiner

SYSTEMS AND METHODS FOR BIOMETRIC TAMPER DETECTION

BACKGROUND OF THE INVENTION

Various embodiments provide systems and methods for detecting tampering with a monitoring device using biometric data.

Large numbers of individuals are currently monitored as part of parole requirements or other requirements. Such monitoring allows a monitoring agency to determine whether the individual is engaging in acceptable patterns of behavior, and where an unacceptable behavior is identified to stop such behavior going forward.

Thus, there exists a need in the art for more advanced approaches, devices and systems for monitoring.

BRIEF SUMMARY OF THE INVENTION

Various embodiments provide systems and methods for detecting tampering with a monitoring device using biometric data.

This summary provides only a general outline of some embodiments. Many other objects, features, advantages and other embodiments will become more fully apparent from the following detailed description, the appended claims and the accompanying drawings and figures.

BRIEF DESCRIPTION OF THE DRAWINGS

A further understanding of the various embodiments may be realized by reference to the figures which are described in remaining portions of the specification. In the figures, similar reference numerals are used throughout several drawings to refer to similar components. In some instances, a sub-label consisting of a lower-case letter is associated with a reference numeral to denote one of multiple similar components. When reference is made to a reference numeral without specification to an existing sub-label, it is intended to refer to all such multiple similar components.

DETAILED DESCRIPTION OF THE INVENTION

Figure 1A:
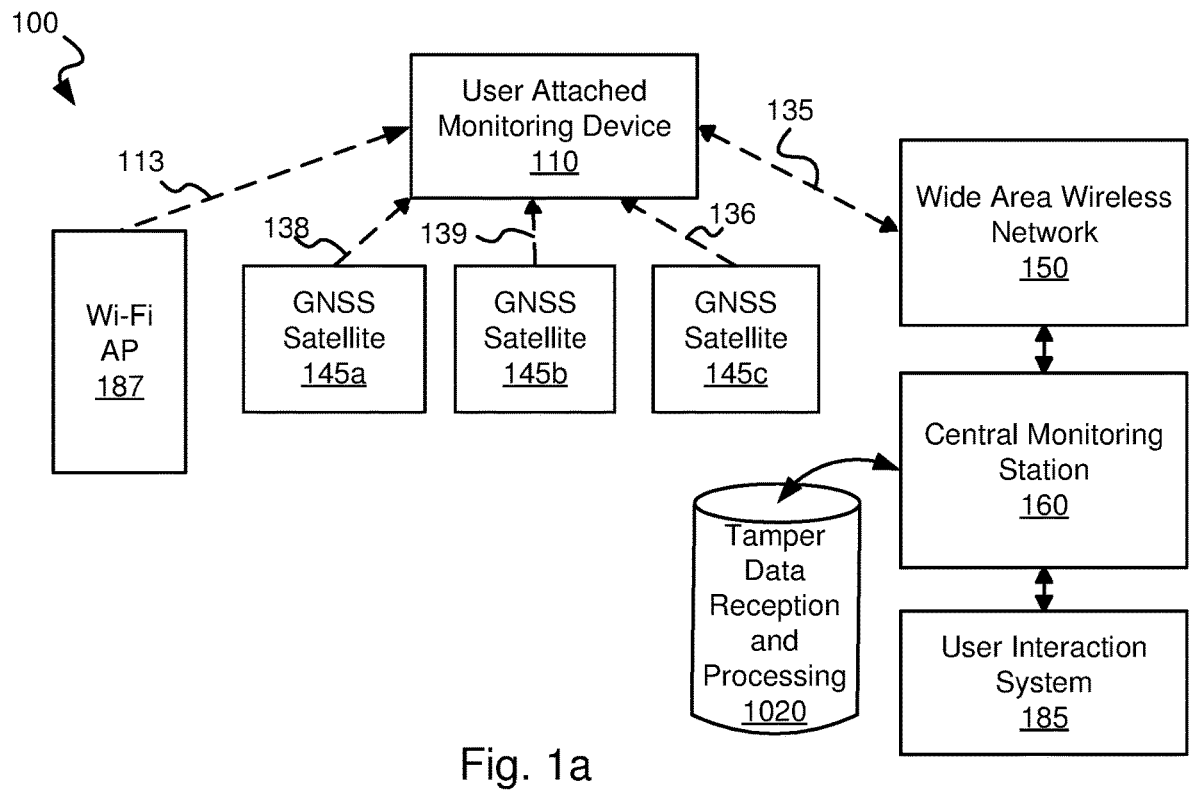
FIG. 1a is a block diagram illustrating a monitoring system including a user attached monitor device and a central monitoring station in accordance with various embodiments.

Various embodiments provide systems and methods for providing check-in services for monitored individuals.

It has been found that returning offenders to society after being locked up in a secure facility with little if any control of their day to day activities is often unsuccessful. It is often helpful to have, for example, a parole officer monitors their movements and activities for a period of time as they reenter society. In some cases, the parole officer is aided by a tracking device attached to the individual being monitored. However, this is costly as a parole officer must be significantly involved in monitoring and responding to situations. Some embodiments disclosed herein reduce the interaction between the tracking device and the parole officer.

Various embodiments provide methods for monitoring that include providing a user attached monitor device. The user attached monitor device includes: a strap operable to secure the user attached monitor device to a wrist of a monitored individual; a first sensor for detecting a sensed, passive biometric data; and a second sensor for detecting a sensed, active biometric data. In some cases, the first sensor includes one or more of: a pulse sensor; a blood oxygen sensory, a proximity sensor, a body temperature sensor, and/or a motion sensor. The method further includes: receiving the sensed, passive biometric data; based at least in part upon the sensed, passive biometric data, requesting the monitored individual engage the user attached monitor device to enable the second sensor to sense the sensed, active biometric data; and determining a tamper status of the user attached monitor device based at least in part on at least one of the sensed, passive biometric data and the sensed, active biometric data. In some instances of the aforementioned embodiments, the methods further include reporting the tamper status to a central monitor station via a wireless communication network.

In various instances of the aforementioned embodiments, the sensed, passive biometric data is a pulse rate of the monitored individual. In some instances of the aforementioned embodiments, the sensed, active biometric data is one or more of: a finger print of the monitored individual, a face image of the monitored individual, and/or an electrocardiogram of the monitored individual. In some cases, the first sensor is a pulse sensor. In various cases, the second sensor includes one or more of: a finger print sensor, an image sensor, and/or an electrocardiogram sensor.

In some instances of the aforementioned embodiments, the user attached monitor device further includes a continuity-based tamper sensor including a conductive element (e.g., electrically conductive and/or optically conductive) extending through the strap. In some such instances, the methods further include: detecting a continuity status using the continuity-based tamper sensor; and determining the tamper status of the user attached monitor device based at least in part on a combination of the continuity status and at least one of the sensed, passive biometric data and the sensed, active biometric data. In various instances of the aforementioned embodiments, the requesting the monitored individual engage the user attached monitor device includes alerting the monitored individual of a requested test via one or more of: a display on the user attached monitor device; a vibrator on the user attached monitor device; and a speaker on the user attached monitor device. In some instances of the aforementioned embodiments, requesting the monitored individual engage the user attached monitor device includes instructions provided via the display of the user attached monitor device guiding the monitored individual on how to engage the user attached monitor device to perform the requested test.

Other embodiments provide monitoring systems that include a user attached monitor device. The user attached monitor device includes: a strap configured to secure the user attached monitor device to a wrist of a monitored individual; a first sensor for detecting a sensed, passive biometric data; a second sensor for detecting a sensed, active biometric data; a processor; and a computer readable medium. The computer readable medium includes non-transitory instructions executable by the processor to: receive the sensed, passive biometric data; based at least in part upon the sensed, passive biometric data, requesting the monitored individual engage the user attached monitor device to enable the second sensor to sense the sensed, active biometric data; and determine a tamper status of the user attached monitor device based at least in part on at least one of the sensed, passive biometric data and the sensed, active biometric data. In some cases, the first sensor includes one or more of: a pulse sensor; a blood oxygen sensor, a proximity sensor, a body temperature sensor, and/or a motion sensor.

Turning to FIG. 1a, a block diagram illustrates a monitoring system 100 including a user attached monitor device 110 and a central monitoring station 160. Central monitoring station 160 is wirelessly coupled to user attached monitor device 110 via one or more wide area wireless (e.g., cellular telephone network, Internet via a Wi-Fi access point, or the like) communication networks 150.

Central monitoring station 160 may be any location, device or system where location data and/or other types of data are received, including by way of non-limiting example: a cellular/smart phone, an email account, a website, a network database, and a memory device. The location data and/or other types of data are stored by central monitoring station 160 and is retrievable by a monitor, such as a parent, guardian, parole officer, court liaison, spouse, friend, or other authorized group or individual. In this manner, the monitor is able to respond appropriately to detected activity of a monitored individual. In some cases, the monitor is able to retrieve the location data and/or other data types via a user interaction system 185 which may be, but is not limited to, a network connected user interface device communicatively coupled via a network to central monitoring station 160 and/or directly to user attached monitor device 110 via wide area wireless network 150.

Central monitoring station 160 may include a server supported website, which may be supported by a server system comprising one or more physical servers, each having a processor, a memory, an operating system, input/output interfaces, and network interfaces, all known in the art, coupled to the network. The server supported website comprises one or more interactive web portals through which the monitor may monitor the location of the monitored individual in accordance with the described embodiments. In particular, the interactive web portals may enable the monitor to retrieve the location and user identification data of one or more monitored individuals, set or modify 'check-in' schedules, and/or set or modify preferences. The interactive web portals are accessible via a personal computing device, such as for example, a home computer, laptop, tablet, and/or smart phone.

In some embodiments, the server supported website comprises a mobile website or mobile application accessible via a software application on a mobile device (e.g. smart phone). The mobile website may be a modified version of the server supported website with limited or additional capabilities suited for mobile location monitoring.

Central monitoring station 160 is communicably coupled to a tamper detection and processing database 1020. Tamper detection and processing database 1020 includes a variety of data corresponding to a monitored individual including, but not limited to, previous tamper status, device health reports, and/or previously indicated possible device errors and possible device tampers. Based upon the disclosure provided herein, one of ordinary skill in the art will recognize other data related to a monitored individual that may be maintained in tamper detection and processing database 1020. In addition, tamper detection and processing database 1020 may include instructions executable by central monitoring station 160 to effectuate various monitoring and/or recording processes that may be executed on central monitoring station 160 and/or downloaded to user attached monitor device 110 for execution by local user attached monitor device 110.

User attached monitor device 110 includes a location sensor that senses the location of the device and generates a location data. For example, when user attached monitor device 110 is capable of receiving wireless global navigation satellite system (hereinafter "GNSS") location information 136, 138, 139 from a sufficient number of GPS or GNSS satellites 145 respectively, user attached monitor device may use the received wireless GNSS location information to calculate or otherwise determine the location of a human subject to whom user attached monitor device 110 is attached. Global positioning system (hereinafter "GPS") is one example of a GNSS location system. While GPS is used in the specific embodiments discussed herein, it is recognized that GPS may be replaced by any type of GNSS system. In some instances, this location includes latitude, longitude, and elevation. It should be noted that other types of earth-based triangulation may be used in accordance with different embodiments of the present invention. For example, other cell phone-based triangulation, UHF band triangulation such as, for example, long range (hereinafter "LoRa") triangulation signals. Based on the disclosure provided herein, one of ordinary skill in the art will recognize other types of earth-based triangulation that may be used. The location data may comprise one or more of, but is not limited to: global positioning system ("GPS") data, Assisted GPS ("A-GPS") data, Advanced Forward Link Trilateration ("AFLT") data, and/or cell tower triangulation data. Where GPS is used, user attached monitor device 110 receives location information from three or more GPS or GNSS satellites 145 via respective communication links 136, 138, 139. The location data and/or other data gathered by user attached monitor device 110 is wirelessly transmitted to central monitoring station 160 via wide area wireless network 150 accessed via a wireless link 135.

In some embodiments, user attached monitor device 110 may further include a biometric tamper detection module 1010 that can, among other things, operate as part of an overall identification sensor generating user identification data for identifying the monitored individual in association with the generation of the location data. The user identification data may comprise one or more of: image data, video data, biometric data (e.g. fingerprint, DNA, retinal scan, facial recognition, electrocardiogram (ECG), or the like), or any other type of data that may be used to verify the identity of the monitored individual at or near the time the location data is generated. The user identification sensor may comprise one or more of: an image sensor camera, microphone, heat sensor, biometric data sensor, or any other type of device capable of sensing/generating the aforementioned types of user identification data. Biometric tamper detection module 1010 assembles one or more elements of data gathered by motion detector 152, microphone 1002, image sensor 1003, pulse/ECG sensor 1001, finger print sensor 1004, and/or an oxygen/temperature sensor 1011 into a user identification package which is forwarded to central monitoring station 160 via wireless transceiver circuitry 168.

Further, biometric tamper detection module 1010 is configured to receive inputs from one or more biometric sensors that are used in combination to determine whether someone has tampered with user attached monitor device 110. In particular, biometric tamper detection module 1010 assembles one or more elements of data gathered by motion detector 152, microphone 1002, image sensor 1003, pulse/ECG sensor 1001, finger print sensor 1004, and/or oxygen/temperature sensor 1011 into a user identification package which is forwarded to central monitoring station 160 via wireless transceiver circuitry 168.

User attached monitor device 110 further includes a memory communicably coupled to a control unit—which is also communicatively coupled to the location sensor, the identification sensor, the biometric tamper detection module, and the wireless transceiver—for controlling the operations thereof in accordance with the functionalities described herein. The memory may include non-transient instructions (e.g., software-based or firmware-based instructions) executable by the control unit to perform and/or enable various functions associated with user attached monitor device 110. User attached monitor device 110 may include a strap (not shown) which can be wrapped around a limb or torso of the monitored individual to secure user attached monitor device 110 to the monitored individual. The strap and/or other parts of user attached monitor device includes one or more tamper circuits and/or sensors that allow for a determination as to whether the device has been removed or otherwise tampered. Examples of a strap and tamper detection circuitry that may be used in relation to various embodiments discussed herein are described in U.S. Pat. No. 9,355,579 entitled "Methods for Image Based Tamper Detection", and filed by Buck et al. on Sep. 15, 2014; and US Pat. Pub. No. US 2017-0270778 A1 entitled "Systems and Methods for Improved Monitor Attachment", and filed by Melton et al. on Mar. 21, 2016. Both of the aforementioned references are incorporated herein by reference for all purposes. Based upon the disclosure provided herein, one of ordinary skill in the art will recognize a variety of straps, tamper circuits, tamper devices, and/or attachment and tamper detection approaches that may be used in relation to various embodiments. User attached monitor device 110 may include a Wi-Fi transceiver capable of receiving information from one or more Wi-Fi access points 187 that may be used to identify location via a Wi-Fi communication link. To perform such WiFi-based location, WiFi receiver 188 scans to identify WiFi access points 187. This scan information is provided to controller circuit 167, which in turn provides the scan information to a third-party geolocation service (not shown) via wide area transceiver 168 and wide area network 150. In turn, the third-party geolocation service returns a location.

Figure 1C:
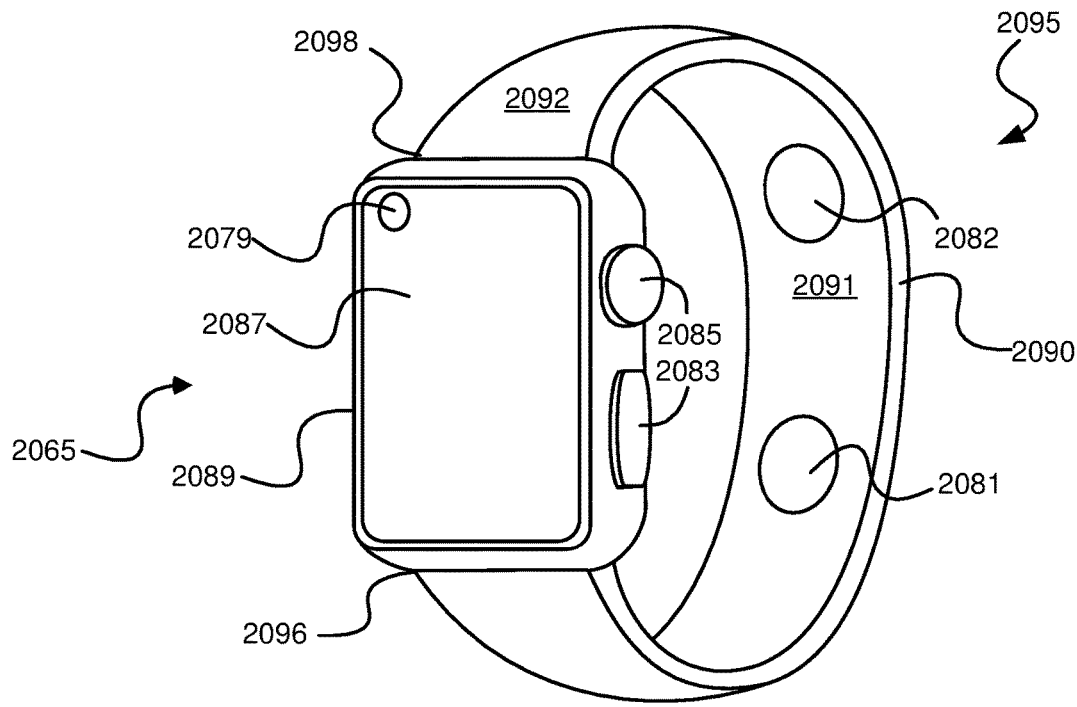
FIG. 1c shows a user attached monitor device with an attachment element for attaching the user attached monitor device to a limb of an individual in accordance with various embodiments.
Figure 1B:
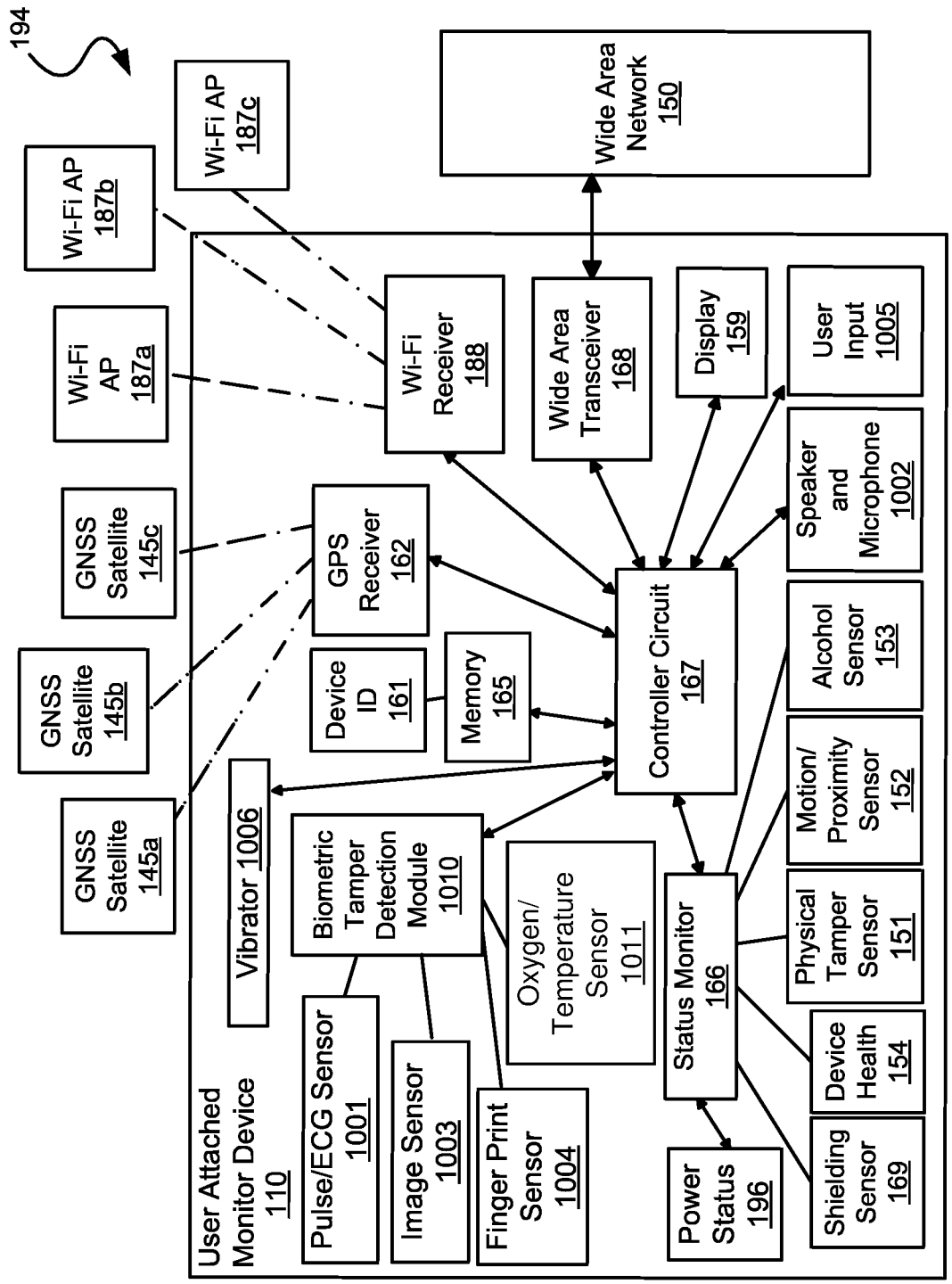
FIG. 1b is a block diagram of a user attached monitor device including a biometric tamper detection module in accordance with some embodiments.

Turning to FIG. 1b, a block diagram 194 of user attached monitor device 110 is shown in accordance with some embodiments. As shown, user attached monitor device 110 includes a device ID 161 that may be maintained in a memory 165, and is thus accessible by a controller circuit 167. Controller circuit 167 is able to interact with a GPS receiver 162 and memory 165 at times for storing and generating records of successively determined location data. Similarly, controller circuit 167 is able to interact with a Wi-Fi receiver 188 and memory 165 at times for storing and generating records of successively determined Wi-Fi access point identifications and signal strength. In some cases, memory 165 may include non-transient instructions (e.g., software-based or firmware-based instructions) executable by controller circuit 167 to perform and/or enable various functions associated with user attached monitor device 110. As user attached monitor device 110 comes within range of one or more Wi-Fi access points (e.g., Wi-Fi access points 187), Wi-Fi receiver 188 senses the signal provided by the respective Wi-Fi access points, and provides an identification of the respective Wi-Fi access point and a signal strength of the signal received from the Wi-Fi access point to Wi-Fi receiver 188. This information is provided to controller circuit 167 which stores the information to memory 165.

Where user attached monitor device 110 is operating in a standard mode, controller circuit 167 causes an update and reporting of the location of user attached monitor device 110 via a wide area transceiver 168 and wide area communication network 150. In some embodiments, wide area transceiver 168 is a cellular telephone transceiver. In some cases, the location data is time stamped. In contrast, where user attached monitor device 110 is within range of a public Wi-Fi access point, reporting the location of user attached monitor device 110 may be done via the public Wi-Fi access point in place of the cellular communication link.

Which technologies are used to update the location of user attached monitor device 110 may be selected either by default, by programming from central monitor station 160, or based upon sensed scenarios with corresponding predetermined selections. For example, it may be determined whether sufficient battery power as reported by power status 196 remains in user attached monitor device 110 to support a particular position determination technology. Where insufficient power remains, the particular technology is disabled. In some cases, a maximum cost of resolving location may be set for user attached monitor device 110. For example, resolving Wi-Fi location data may incur a per transaction cost to have a third-party service provider resolve the location information. When a maximum number of resolution requests have been issued, the Wi-Fi position determination technology may be disabled. Further, it may be determined whether the likelihood that a particular position determination technology will be capable of providing meaningful location information. For example, where user attached monitor device 110 is moved indoors, GPS receiver 162 may be disabled to save power. Alternatively, where the tracking device is traveling at relatively high speeds, the Wi-Fi receiver 188 may be disabled. As yet another example, where cellular phone jamming is occurring, support for cell tower triangulation position determination may be disabled. As yet another example, where GPS jamming is occurring, GPS receiver 162 may be disabled. As yet another example, where user attached monitor device 110 is stationary, the lowest cost (from both a monetary and power standpoint) tracking may be enabled while all other technologies are disabled. Which position determination technologies are used may be based upon a zone in which a tracking device is located. Some zones may be rich in Wi-Fi access points and in such zones Wi-Fi technology may be used. Otherwise, another technology such as cell tower triangulation or GPS may be used. Based upon the disclosure provided herein, one of ordinary skill in the art will recognize other scenarios and corresponding combinations of technologies may be best.

Controller circuit 167 of user attached monitor device 110 at times functions in conjunction with wide area transceiver 168 to send and receive data and signals through wide area communication network 150. This link at times is useful for passing information and/or control signals between a central monitoring system (not shown) and user attached monitor device 110. The information transmitted may include, but is not limited to, location information, tamper information, measured alcohol information, one or more passive or active impairment tests applied to the monitored individual, and information about the status of user attached monitor device 110. Based on the disclosure provided herein, one of ordinary skill in the art will recognize a variety of information that may be transferred via wide area communication network 150.

Various embodiments of user attached monitor device 110 include a variety of sensors capable of determining the status of user attached monitor device 110, and of the individual associated therewith. For example, a status monitor 166 may include one or more of the following subcomponents: power status sensor 196 capable of indicating a power status of user attached monitor device 110, a pulse/ECG sensor 1001 operable to sense pulse rate of the monitored individual and an electrocardiogram unique to the monitored individual based upon electrodes (not shown) in contact with the skin of the monitored individual, an image sensor 1003 (e.g., camera) operable to capture an image of the monitored individual when user attached monitor device 110 is properly positioned, and a finger print sensor 1004 operable to sense the print of a finger placed on a display 159 of user attached monitor device 110. The power status may be expressed, for example, as a percentage of battery life remaining. Based upon the disclosure provided herein, one of ordinary skill in the art will recognize a variety of forms in which power status may be expressed. The pulse rate may be expressed in beats per minute and the ECG may be shown visually via display 159. Based upon the disclosure provided herein, one of ordinary skill in the art will recognize a variety of forms in which pulse rate and/or ECG rate may be expressed.

In addition, user attached monitor device 110 includes a set of shielding sensors 169 that are capable of determining whether user attached monitor device 110 is being shielded from receiving GPS signals and/or if GPS jamming is ongoing, a set of device health indicators 154, a physical tamper sensor 151 capable of determining whether unauthorized access to user attached monitor device 110 has occurred or whether user attached monitor device 110 has been removed from an associated individual being monitored, a motion/proximity sensor 152 capable of determining whether user attached monitor device 110 is moving and/or whether it is within proximity of an individual associated with user detached monitor device 2095, and/or an alcohol sensor 153. Such an alcohol sensor may be any alcohol sensor capable of estimating an amount of alcohol in the individual being monitored. Based upon the disclosure provided herein, one of ordinary skill in the art will recognize a variety of alcohol sensors and corresponding alcohol sensing circuitry that may be used in relation to different embodiments. In some cases, motion/proximity sensor 152 includes one or more accelerometer sensors and/or gyro sensors that are capable of accurately sensing motion of the monitored individual. In some cases, the detected motion information is used to quantify the gait of the monitored individual or balance of the monitored individual as they move or perform a particular task. In addition, motion/proximity sensor 152 includes sensors capable of determining a proximity of user attached monitor device 110 to a monitored individual to which the device is assigned. This information may be used to assure that the monitored individual is wearing user attached monitor device 110. Based on the disclosure provided herein, one of ordinary skill in the art will recognize a variety of shielding sensors, a variety of device health transducers and indicators, a variety of tamper sensors, various different types of motion sensors, different proximity to human sensors, and various human body physical measurement sensors or transducers that may be incorporated into user attached monitor device 110 according to various different instances and/or embodiments.

A user input 1005 allows for a user of user attached monitor device 110 to provide information to user attached monitor device 110. User input 1005 may include a push button, a turning knob, and/or a touchscreen display (integrated as part of display 159) depending upon the particular implementation. A speaker and microphone 1002 are included that are capable of providing an audio sound audible to a user of user attached monitor device 110 and of accepting audio. A vibrator 1006 is included that is capable of making user attached monitor device 110 vibrate to alert a user of user attached monitor device. Each of vibrator 1006, speaker 1002, user input 1005, and display 159 is communicatively coupled to memory 124 and/or a controller circuit 167 for controlling the operations thereof.

A schedule of check-in times (either periodic or random) may be downloaded to memory 165 by central monitoring station 160 via wireless link 135. A monitored individual wearing user attached monitor device 110 may be alerted by one or more of: a visual prompt via display 159, an audio prompt via speaker 1002, and a tactile prompt via vibrator 1006. In various cases, controller circuit 167 is part of an integrated circuit. In one or more cases, memory 165 is included in an integrated circuit with controller circuit 167. In various cases, memory 165 may include non-transient instructions (e.g., software or firmware-based based instructions) executable by controller circuit 167 to perform and/or enable various functions associated with user attached monitor device 110. In some embodiments, alerting the monitored individual involves a prompt that includes an e-mail or text message generated by central monitoring station 160 (e.g. the server supported website) and transmitted to the e-mail account or cellular phone number corresponding to user attached monitor device 110. In particular embodiments, such a prompt may include a 'post' on the user's 'wall,' 'feed,' or other social networking privilege. In some embodiments, the prompt may comprise an automated or live phone call to the monitored individual.

Turning to FIG. 1c, a sensing device 2065 is shown with an example attachment element 2090 connected at opposite ends of sensing device 2065 (i.e., a first end 2096 and a second end 2098). Attachment element 2090 has an outer surface 2092 and an inner surface 2091. Attachment element 2090 is operable to securely attach a user attached monitor device 2095 (i.e., a combination of sensing device 2065 and attachment element 2090) to a limb of an individual in accordance with some embodiments. One or more electrodes 2081, 2082 are formed into inner surface 2091 such that they are in close proximity to the skin of the monitored individual when user attached monitor device 2095 is attached to the monitored individual. In some cases, attachment element 2090 is tailored to attached to a wrist of a monitored individual. In various embodiments, attachment element 2090 includes electrically and/or optically conductive material used to make a conductive connection from first end 2096 to second end 2098 through attachment element 2090 and is used in relation to determining whether user attached monitor device 2095 remains attached and/or has been tampered with. While FIG. 1c shows a strap as an example attachment element, based upon the disclosure provided herein, one of ordinary skill in the art will recognize other types of attachment elements that may be used in relation to different embodiments. In other embodiments, attachment element 2090 is long enough to attach around the torso of the monitored individual and is sufficiently flexible to allow expansion and contraction of the chest of the monitored individual as they breath. Such expansion and contraction may be used to sense respiration rate of the monitored individual.

Sensing device 2065 includes a case 2089 in which various electronic components are maintained. In addition, sensing device 2065 includes a button 2083, a radial dial 2085, a display 2087 (which may be a touchscreen display), and a combination speaker, microphone, and image sensor 2079. Together, sensing device 2065 includes a button 2083, a radial dial 2085, a display 2087, a combination speaker, microphone, and image sensor 2079, electrodes 2081, 2082 provide the user interface for user attached monitor device 2065 and support the functionality of the various sensors discussed above in relation to FIG. 1b. Based upon the disclosure provided herein, one of ordinary skill in the art will recognize a variety of inputs and outputs that may be incorporated into user attached monitor device 2095 to provide the functionality discussed herein.

Figure 2:
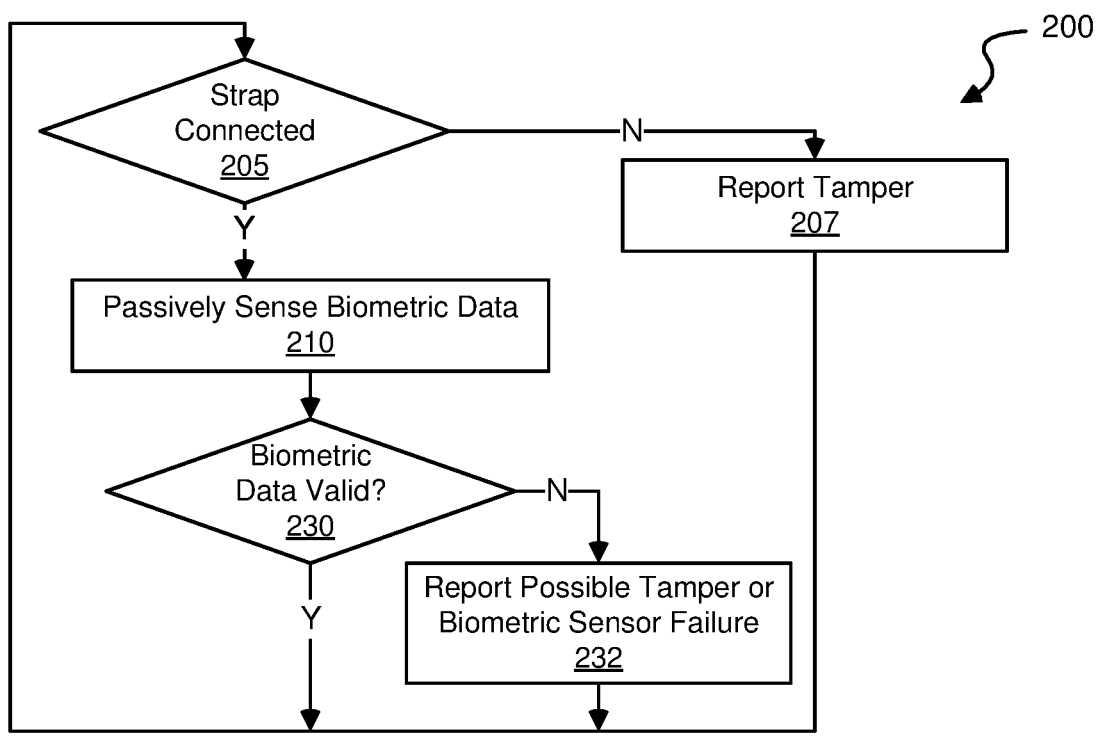
FIG. 2 is a flow diagram showing a method for tamper detection using a combination of strap continuity and one or more biometrically sensed data in accordance with one or more embodiments.

Turning to FIG. 2, a flow diagram 200 shows a method for tamper detection using a combination of strap continuity and one or more biometrically sensed data in accordance with one or more embodiments. Following flow diagram 200, it is determined whether a continuity circuit in a strap securing a user attached monitor device 110 to a limb of a monitored individual indicates that the strap is properly connected (block 205). As discussed above, some embodiments of user attached monitor device 110 includes a tamper sensor that detects a charge or senses a light passing through an electrically and/or optically conductive material used to make a conductive connection from a first end of the strap to a second end of the strap. When the strap is properly connected around the limb of the monitored individual, a charge placed on one end of the strap is detected on the other end of the strap (or a light placed on one end of the strap is visible at the other end of the strap). Thus, determining whether the strap is connected includes determining whether the expected charge or light placed on one end of the strap is sensed on the other end of the strap. Where the charge or light is not sensed, the strap is considered disconnected. Alternatively, where the charge or light is detected, the strap is considered connected. While this embodiment is discussed as using a continuity-based approach to determine strap connection, based upon the disclosure provided herein, one of ordinary skill in the art will recognize other approaches for determining whether a strap is connected that may be used in relation to different embodiments.

Where the strap is determined to have been disconnected or cut (block 205), a tamper is reported (block 207). Reporting the tamper may include storing information associated with the tamper to a memory local to user attached monitor device 110, and when desired transmitting that information to central monitor station 160 via wireless wide area network 150. In some cases, the tamper information is immediately transmitted. In other cases, the tamper information is transmitted at a predetermined communication time along with other information that is to be transmitted. The tamper information may include, but is not limited to, a time stamp indicating when the tamper condition was detected, and the cause of the tamper (e.g., strap disconnected). Based upon the disclosure provided herein, one of ordinary skill in the art will recognize a variety of information that may be transmitted as part of the tamper information.

Alternatively, where the strap is determined not to have been disconnected or cut (block 205), biometric data is passively sensed (block 210). Some biometric data, such as, for example, pulse rate, can be sensed without alerting the monitored individual and requiring them to engage in a biometric test. The passively sensed biometric data is tested to determine if it is valid (block 230). Thus, for example, where the sensed biometric data is a pulse rate, the sensed pulse rate data is compared with both a lower value and an upper value to assure that the sensed data is within a range of possible pulse rates. The upper and lower values of the range may be specifically selected for the monitored individual, or may be generic values for a large population of individuals. Based upon the disclosure provided herein, one of ordinary skill in the art will recognize other passively obtained biometric data and/or comparison ranges that can be used to validate the sensed data.

Where the sensed biometric data is not valid (block 230), a possible tamper, strap connected sensor, or biometric sensor failure is reported (block 232). Again, the reporting may include storing information associated with the tamper to a memory local to user attached monitor device 110, and when desired transmitting that information to central monitor station 160 via wireless wide area network 150. The tamper information may include, but is not limited to, a time stamp indicating when the tamper condition was detected, and the cause of the tamper (e.g., strap connected, but invalid biometric data sensed). Thus, for example, where the biometric data is a pulse rate, the tamper information may include, but is not limited to, a time stamp indicating when the tamper condition was detected, the cause of the tamper (e.g., strap connected, but pulse rate outside of an expected range), and the sensed pulse rate. Based upon the disclosure provided herein, one of ordinary skill in the art will recognize a variety of information that may be transmitted as part of the tamper information.

Figure 3:
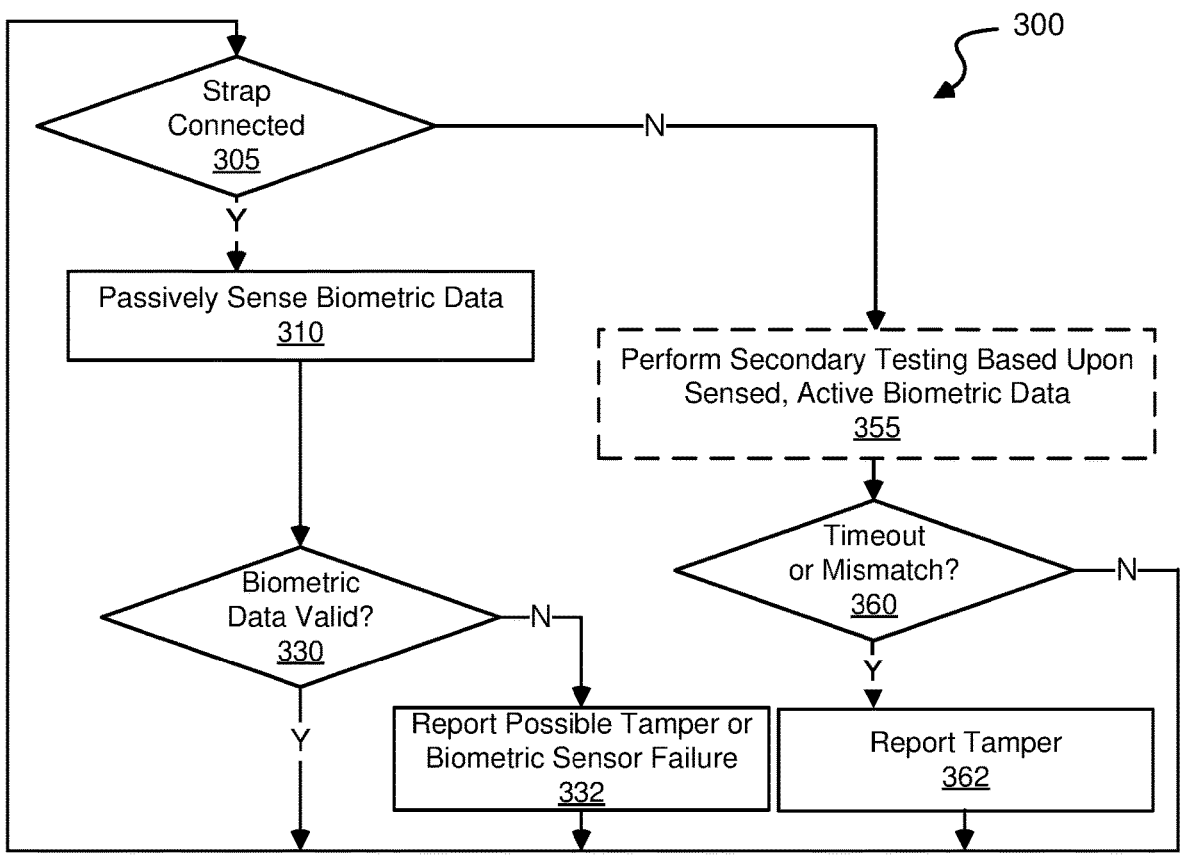
FIG. 3 is a flow diagram 300 shows a method for tamper detection using a combination of strap continuity, a passive biometric data, and an active biometric data in accordance with some embodiments

Turning to FIG. 3, a flow diagram 300 shows a method for tamper detection using a combination of strap continuity, a passive biometric data, and an active biometric data in accordance with some embodiments. Following flow diagram 300, it is determined whether a continuity circuit in a strap securing a user attached monitor device 110 to a limb of a monitored individual indicates that the strap is properly connected (block 305). As discussed above, some embodiments of user attached monitor device 110 includes a tamper sensor that detects a charge or senses a light passing through an electrically and/or optically conductive material used to make a conductive connection from a first end of the strap to a second end of the strap. When the strap is properly connected around the limb of the monitored individual, a charge placed on one end of the strap is detected on the other end of the strap (or a light placed on one end of the strap is visible at the other end of the strap). Thus, determining whether the strap is connected includes determining whether the expected charge or light placed on one end of the strap is sensed on the other end of the strap. Where the charge or light is not sensed, the strap is considered disconnected. Alternatively, where the charge or light is detected, the strap is considered connected. While this embodiment is discussed as using a continuity-based approach to determine strap connection, based upon the disclosure provided herein, one of ordinary skill in the art will recognize other approaches for determining whether a strap is connected that may be used in relation to different embodiments.

Where the strap is determined to have been disconnected or cut (block 305), secondary testing based upon sensed, active biometric data is performed (block 355). As used herein, the phrase "active biometric data" is biometric data that is gathered upon active participation by the monitored individual. As used herein, the phrase "passive biometric data" is biometric data that is gathered without active participation by the monitored individual. As an example, "active biometric data" may include an image of a monitored individual's face that is collected after alerting the monitored individual to take an image of their face using an image sensor on a user attached monitor device. As another example, "passive biometric data" may include an image of a monitored individual's face that is collected without alerting the monitored individual that an image is being taken, but rather by monitoring information presented to the image sensor and automatically capturing an image of the monitored individual whenever user attached monitor device 110 is oriented such that a face is within view of the image sensor of user attached monitor device 110. As another example, "passive biometric data" may include a pulse rate of a monitored individual that is automatically sensed using sensors in user attached monitor device 110. As yet another example, "active biometric data" may include a finger print of a monitored individual that is collected after alerting the monitored individual to take a finger print using user attached monitor device 110. As yet a further example, "passive biometric data" may include an ECG of a monitored individual that is automatically sensed using sensors in user attached monitor device 110. As yet another example, "active biometric data" may include an ECG of a monitored individual that is collected after alerting the monitored individual to take an ECG using user attached monitor device 110. Based upon the disclosure provided herein, one of ordinary skill in the art will recognize a variety of active and passive sensed biometric data that may be used in relation to different embodiments. Block 335 is shown in dashed lines as it includes a variety of functions and/or processes that are further discussed below in relation to FIGS. 5-8.

The processes of block 355 return either: (1) a "Timeout" condition indicating that the monitored individual failed to engage in the alerted active biometric data gathering within an allowed time period, (2) a "Mismatch" condition indicating that the sensed, active biometric data did not match what was expected, or (3) a "Match" condition indicating that the sensed, active biometric data matched what was expected. These conditions are further discussed below in relation to FIGS. 5-8. It is determined whether a Timeout or Mismatch condition was returned from the secondary testing of block 355 (block 360). Where either a Timeout or a Mismatch condition is returned (block 360), a tamper is reported (block 362). Reporting the tamper may include storing information associated with the tamper to a memory local to user attached monitor device 110, and when desired transmitting that information to central monitor station 160 via wireless wide area network 150. In some cases, the tamper information is immediately transmitted. In other cases, the tamper information is transmitted at a predetermined communication time along with other information that is to be transmitted. The tamper information may include, but is not limited to, a time stamp indicating when the tamper condition was detected, and the cause of the tamper (e.g., strap disconnected and Mismatch condition, or strap disconnected and Timeout condition). Based upon the disclosure provided herein, one of ordinary skill in the art will recognize a variety of information that may be transmitted as part of the tamper information.

Alternatively, where the strap is determined not to have been disconnected or cut (block 305), biometric data is passively sensed (i.e., sensed, passive biometric data)(block 310). As used herein, "sensed, passive biometric data" is used in its broadest sense to mean biometric data sensed from an individual wearing a sensing device without alerting the monitored individual and requiring them to engage in a biometric test. As just some examples, sensed, passive biometric data may include, but is not limited to, a pulse rate, a blood oxygen level, an external body temperature, motion of the body, and/or proximity of a sensing device to the body of the monitored individual. The passively sensed biometric data is tested to determine if it is valid (block 330). Thus, for example, where the sensed biometric data is a pulse rate, the sensed pulse rate data is compared with both a lower value and an upper value to assure that the sensed data is within a range of possible pulse rates. The upper and lower values of the range may be specifically selected for the monitored individual, or may be generic values for a large population of individuals. Based upon the disclosure provided herein, one of ordinary skill in the art will recognize other passively obtained biometric data and/or comparison ranges that can be used to validate the sensed data.

Where the sensed, passive biometric data is not valid (block 330), a possible tamper or biometric sensor failure is reported (block 332). Again, the reporting may include storing information associated with the tamper to a memory local to user attached monitor device 110, and when desired transmitting that information to central monitor station 160 via wireless wide area network 150. The tamper information may include, but is not limited to, a time stamp indicating when the tamper condition was detected, and the cause of the tamper (e.g., strap connected, but invalid biometric data sensed). Thus, for example, where the biometric data is a pulse rate, the tamper information may include, but is not limited to, a time stamp indicating when the tamper condition was detected, the cause of the tamper (e.g., strap connected, but pulse rate outside of an expected range), and the sensed pulse rate. Based upon the disclosure provided herein, one of ordinary skill in the art will recognize a variety of information that may be transmitted as part of the tamper information.

Figure 4:
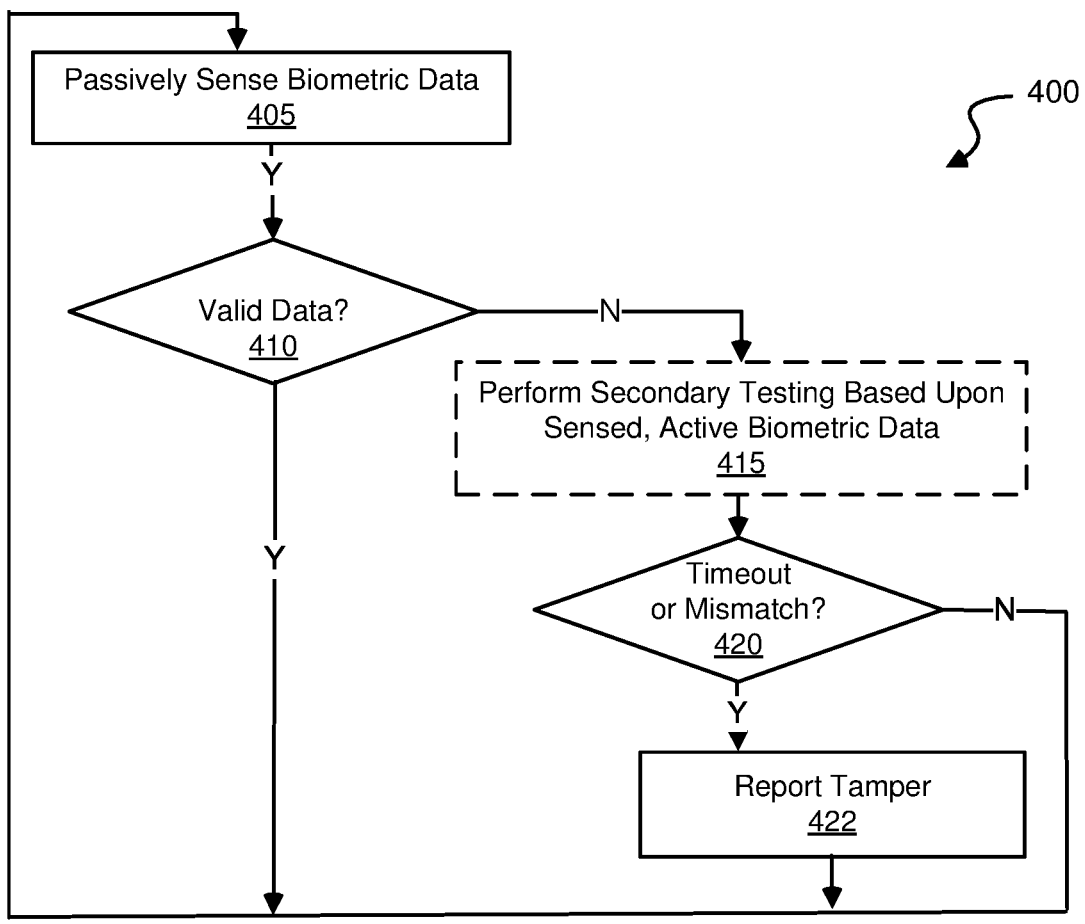
FIG. 4 is a flow diagram showing a method for tamper detection using a combination of at least one sensed, passive biometric data and at least one sensed, active biometric data in accordance with one or more embodiments.

Turning to FIG. 4, a flow diagram 400 shows a method for tamper detection using a combination of at least one sensed, passive biometric data and at least one sensed, active biometric data in accordance with one or more embodiments. Following flow diagram 400, biometric data is passively sensed (i.e., sensed, passive biometric data)(block 405). As just some examples, sensed, passive biometric data may include, but is not limited to, a pulse rate, a blood oxygen level, an external body temperature, motion of the body, and/or proximity of a sensing device to the body of the monitored individual. Some biometric data, such as, for example, pulse rate, can be sensed without alerting the monitored individual and requiring them to engage in a biometric test. The passively sensed biometric data is tested to determine if it is valid (block 410). Thus, for example, where the sensed biometric data is a pulse rate, the sensed pulse rate data is compared with both a lower value and an upper value to assure that the sensed data is within a range of possible pulse rates. The upper and lower values of the range may be specifically selected for the monitored individual, or may be generic values for a large population of individuals. Based upon the disclosure provided herein, one of ordinary skill in the art will recognize other passively obtained biometric data and/or comparison ranges that can be used to validate the sensed data.

Where the sensed, passive biometric data is not valid (block 410), secondary testing based upon sensed, active biometric data is performed (block 415). Block 415 is shown in dashed lines as it includes a variety of functions and/or processes that are further discussed below in relation to FIGS. 5-8. As used herein, "sensed, active biometric data" is used in its broadest sense to mean biometric data sensed from an individual wearing a sensing device after alerting the monitored individual and requiring them to engage in a biometric test. In some cases, enhanced or additional biometric data can be achieved with the aid of the monitored individual. Based upon the disclosure provided herein, one of ordinary skill in the art will recognize a variety of biometric data that may be sensed after alerting a monitored individual. The processes of block 355 return either: (1) a "Timeout" condition indicating that the monitored individual failed to engage in the alerted active biometric data gathering within an allowed time period, (2) a "Mismatch" condition indicating that the sensed, active biometric data did not match what was expected, or (3) a "Match" condition indicating that the sensed, active biometric data matched what was expected. These conditions are further discussed below in relation to FIGS. 5-8.

It is determined whether a Timeout or Mismatch condition was returned from the secondary testing of block 415 (block 420). Where either a Timeout or a Mismatch condition is returned (block 420), a tamper is reported (block 422). Reporting the tamper may include storing information associated with the tamper to a memory local to user attached monitor device 110, and when desired transmitting that information to central monitor station 160 via wireless wide area network 150. In some cases, the tamper information is immediately transmitted. In other cases, the tamper information is transmitted at a predetermined communication time along with other information that is to be transmitted. The tamper information may include, but is not limited to, a time stamp indicating when the tamper condition was detected, and the cause of the tamper (e.g., no pulse rate and Mismatch condition, pulse rate out of range and Mismatch condition, no pulse rate and Timeout condition, or pulse rate out of range and Timeout condition). Based upon the disclosure provided herein, one of ordinary skill in the art will recognize a variety of information that may be transmitted as part of the tamper information.

Figure 5:
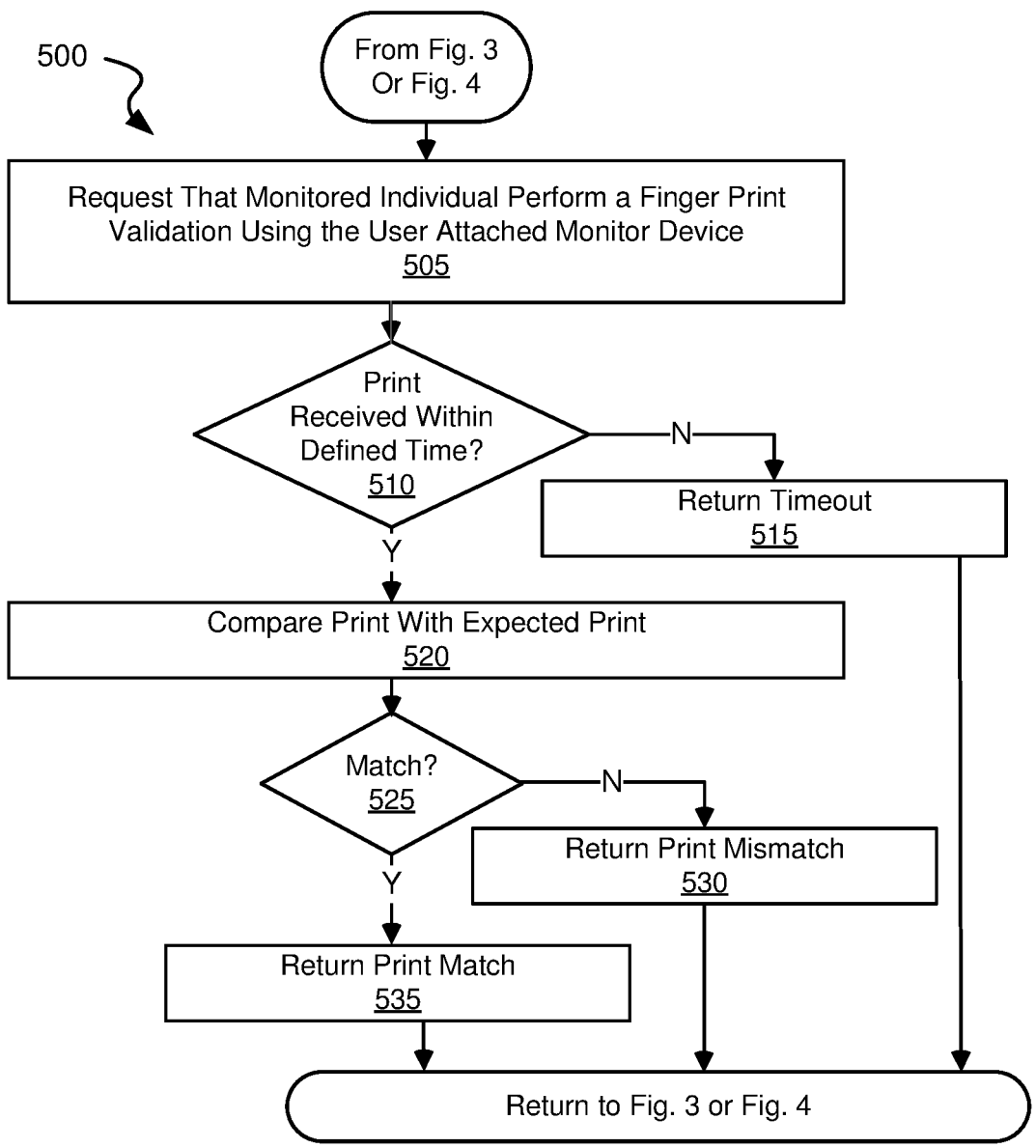
FIG. 5 is a flow diagram showing the tamper detection method of FIG. 3 or FIG. 4 tailored to use finger print recognition as secondary testing using sensed, active biometric data in accordance with various embodiments.

Turning to FIG. 5, a flow diagram 500 shows a tamper detection method implementing block 355 of FIG. 3 or block 415 of FIG. 4 tailored to use finger print recognition as secondary testing using sensed, active biometric data in accordance with some embodiments. Following flow diagram 500, a request is made to a monitored individual to perform finger print validation using a user attached monitor device 110 (block 505). The request may be made by, for example, alerting the monitored individual of the need to engage in secondary testing, and requesting that the monitored individual engage the finger print functionality of user attached monitor device 110. The request may include detailed instructions for how to provide finger print data including, for example, placing their finger within view of image sensor 1003 of user attached monitor device 110. The alert may be done by displaying a message to the monitored individual that may be visible via the display of user attached monitor device 110. This message may be automatically generated and displayed whenever secondary testing is requested. Alternatively, or in addition, an audible alarm via speaker 1002 and/or a tactile alarm via vibrator 1006 may be generated to cause the monitored individual to look at the display of user attached monitor device. Based upon the disclosure provided herein, one of ordinary skill in the art will recognize a variety of messages, instructions, and/or alerts that may be used to encourage the monitored individual to engage in the requested gathering of sensed, active biometric data in accordance with different embodiments.

It is determined whether the finger print of the monitored individual is received within a defined timeout period (block 510). In some cases, the monitored individual is given a fixed amount of time (e.g., two minutes) to provide the requested finger print via user attached monitor device 110. Where the finger print is not received within a timeout period (block 510), a Timeout condition is returned (block 515).

Alternatively, where the finger print is timely received (block 510), the received finger print is compared with an expected finger print (block 520). The expected finger print may be taken at the time that user attached monitor device 110 was assigned to the monitored individual, and then stored in memory 165 of user attached monitor device 110. In some cases, the expected finger print is gathered in the same way that the finger print is gathered when the monitored individual is responding to a request for a finger print during a tamper monitoring operation. Based upon the disclosure provided herein, one of ordinary skill in the art will recognize a variety of finger print gathering processes that may be used in relation to user attached monitor device 110, and/or finger print comparison processes that may be used to determine whether a gathered finger print matches an expected finger print in accordance with different embodiments.

Where the sensed finger print does not match the expected finger print (block 525), a Mismatch condition is returned (block 530). Alternatively, where the sensed finger print matches the expected finger print (block 525), a Match condition is returned (block 535). As discussed above in relation to FIG. 3 and FIG. 4, the respective Timeout condition, Mismatch condition, and Match condition dictate the generation of a tamper indication and corresponding tamper notification.

Figure 6:
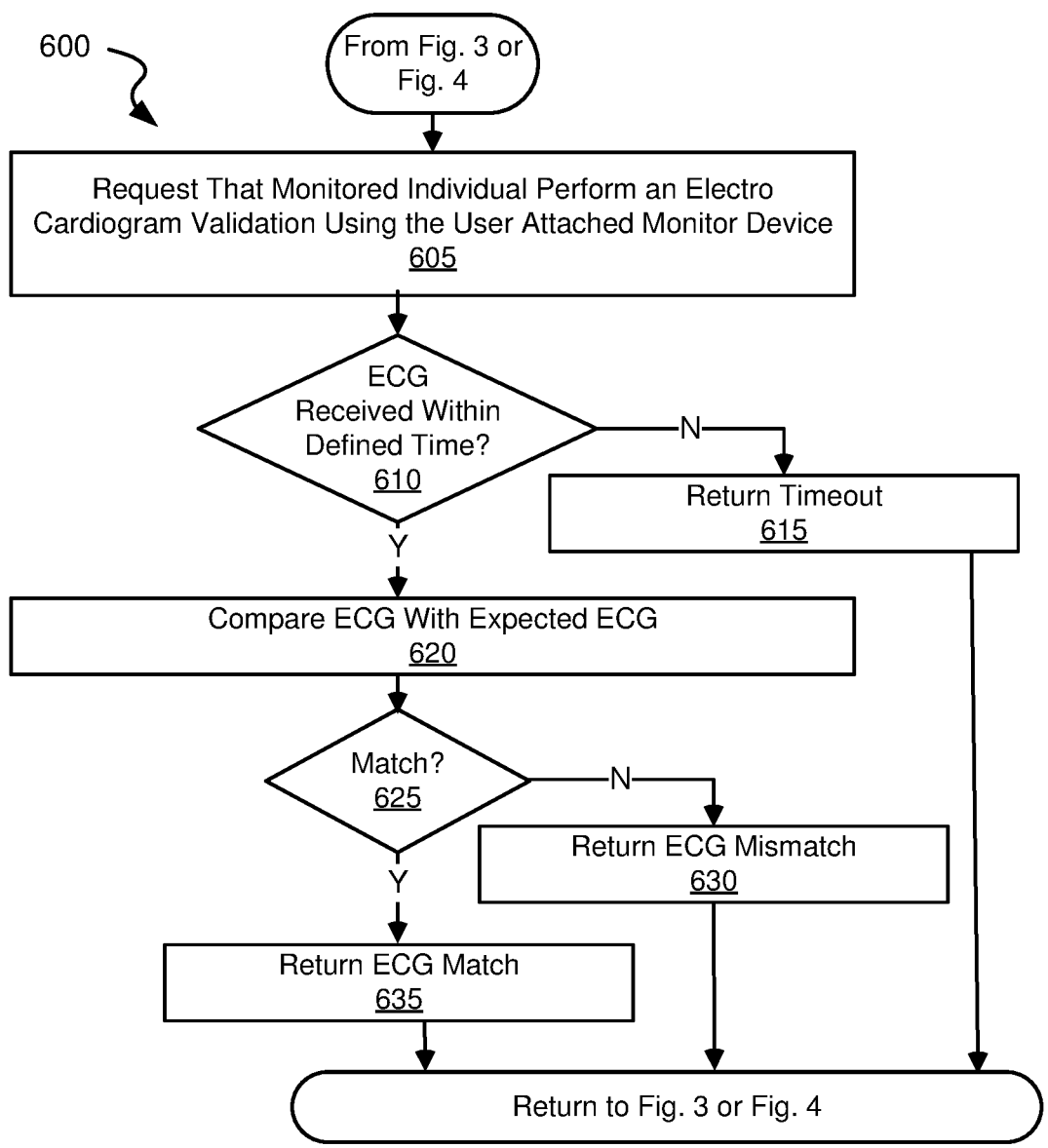
FIG. 6 is a flow diagram showing the tamper detection method of FIG. 3 or FIG. 4 tailored to use electrocardiogram recognition as secondary testing using sensed, active biometric data in accordance with some embodiments.

Turning to FIG. 6, a flow diagram 600 shows another tamper detection method implementing block 355 of FIG. 3 or block 415 of FIG. 4 tailored to use electrocardiogram recognition as secondary testing using sensed, active biometric data in accordance with some embodiments. Following flow diagram 600, a request is made to a monitored individual to perform ECG validation using a user attached monitor device 110 (block 605). The request may be made by, for example, alerting the monitored individual of the need to engage in secondary testing, and requesting that the monitored individual engage the ECG functionality of user attached monitor device 110. The request may include detailed instructions for how to provide ECG data including, for example, holding a strap including ECG electrodes near the skin of the monitored individual. The alert may be done by displaying a message to the monitored individual that may be visible via the display of user attached monitor device 110. This message may be automatically generated and displayed whenever secondary testing is requested. Alternatively, or in addition, an audible alarm via speaker 1002 and/or a tactile alarm via vibrator 1006 may be generated to cause the monitored individual to look at the display of user attached monitor device. Based upon the disclosure provided herein, one of ordinary skill in the art will recognize a variety of messages, instructions, and/or alerts that may be used to encourage the monitored individual to engage in the requested gathering of sensed, active biometric data in accordance with different embodiments.

It is determined whether the ECG data of the monitored individual is received within a defined timeout period (block 610). In some cases, the monitored individual is given a fixed amount of time (e.g., five minutes) to provide the requested ECG data via user attached monitor device 110. Where the ECG data is not received within a timeout period (block 610), a Timeout condition is returned (block 615).

Alternatively, where the ECG data is timely received (block 610), the received ECG data is compared with an expected ECG data (block 620). The expected ECG data may be taken at the time that user attached monitor device 110 was assigned to the monitored individual, and then stored in memory 165 of user attached monitor device 110. In some cases, the expected ECG data is gathered in the same way that the ECG data is gathered when the monitored individual is responding to a request for ECG data during a tamper monitoring operation. Based upon the disclosure provided herein, one of ordinary skill in the art will recognize a variety of ECG gathering processes that may be used in relation to user attached monitor device 110, and/or ECG data comparison processes that may be used to determine whether gathered ECG data matches an expected ECG data in accordance with different embodiments.

Where the sensed ECG data does not match the expected ECG data (block 625), a Mismatch condition is returned (block 630). Alternatively, where the sensed ECG data matches the expected ECG data (block 625), a Match condition is returned (block 635). As discussed above in relation to FIG. 3 and FIG. 4, the respective Timeout condition, Mismatch condition, and Match condition dictate the generation of a tamper indication and corresponding tamper notification.

Figure 7:
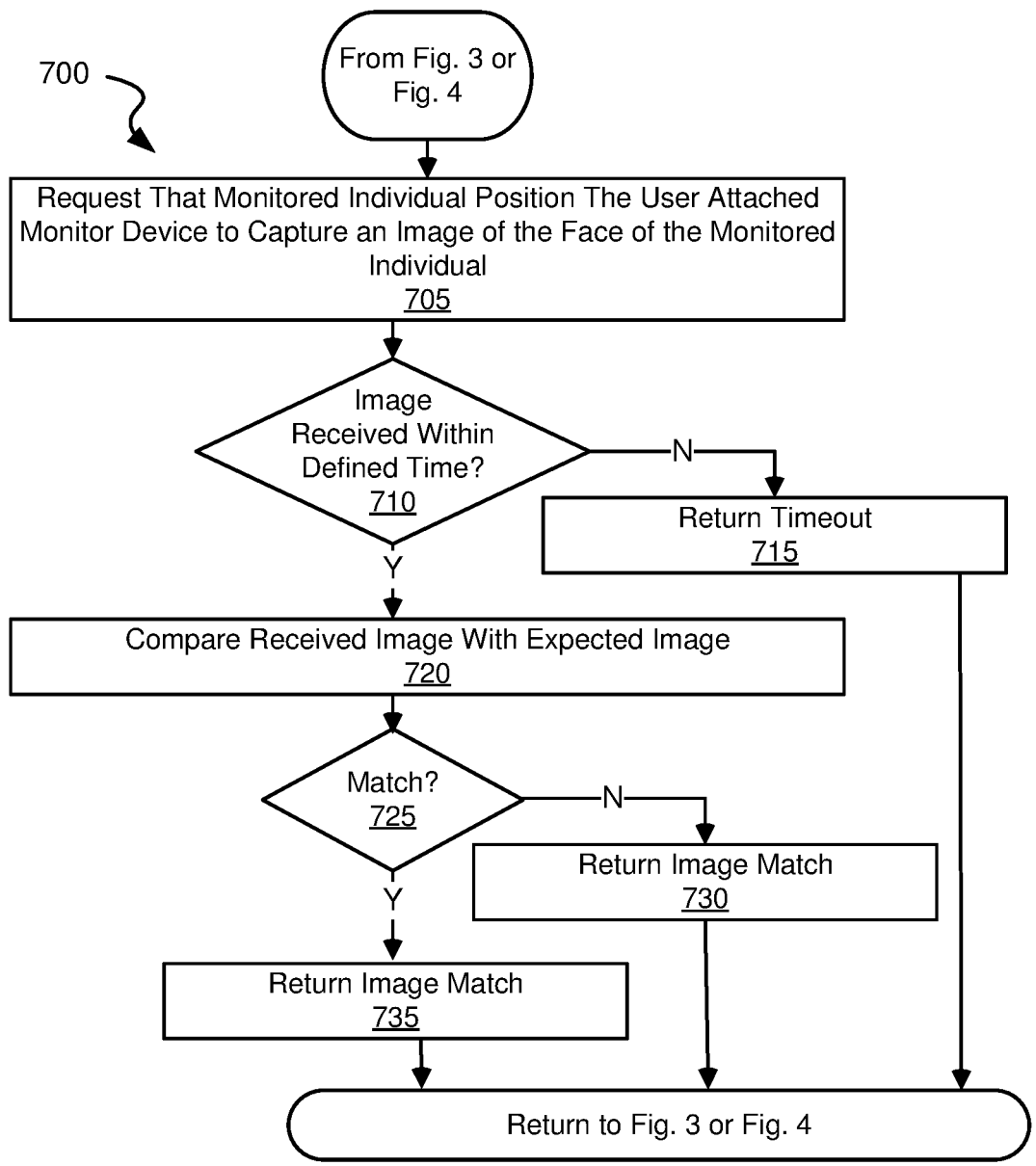
FIG. 7 is a flow diagram showing the tamper detection method of FIG. 3 or FIG. 4 tailored to use facial recognition as secondary testing using sensed, active biometric data in accordance with various embodiments.

Turning to FIG. 7, a flow diagram 700 shows yet another tamper detection method implementing block 355 of FIG. 3 or block 415 of FIG. 4 tailored to use facial recognition as secondary testing using sensed, active biometric data in accordance with various embodiments. Following flow diagram 700, a request is made to a monitored individual to perform facial validation using a user attached monitor device 110 (block 705). The request may be made by, for example, alerting the monitored individual of the need to engage in secondary testing, and requesting that the monitored individual capture an image of their face using user attached monitor device 110. The request may include detailed instructions for how to capture a face image including, for example, holding their arm such that an image sensor in user attached monitor device 110 is oriented to capture an image of the monitored individual's face. The alert may be done by displaying a message to the monitored individual that may be visible via the display of user attached monitor device 110. This message may be automatically generated and displayed whenever secondary testing is requested. Alternatively, or in addition, an audible alarm via speaker 1002 and/or a tactile alarm via vibrator 1006 may be generated to cause the monitored individual to look at the display of user attached monitor device. Based upon the disclosure provided herein, one of ordinary skill in the art will recognize a variety of messages, instructions, and/or alerts that may be used to encourage the monitored individual to capture a face image in the requested gathering of sensed, active biometric data in accordance with different embodiments.

It is determined whether the face image of the monitored individual is received within a defined timeout period (block 710). In some cases, the monitored individual is given a fixed amount of time (e.g., two minutes) to provide the requested face image via user attached monitor device 110. Where the face image is not received within a timeout period (block 710), a Timeout condition is returned (block 715).

Alternatively, where the face image is timely received (block 710), the received face image is compared with an expected face image (block 720). The expected face image may be taken at the time that user attached monitor device 110 was assigned to the monitored individual, and then stored in memory 165 of user attached monitor device 110. In some cases, the expected face image is captured in the same way that the face image is gathered when the monitored individual is responding to a request for a face image during a tamper monitoring operation. Based upon the disclosure provided herein, one of ordinary skill in the art will recognize a variety of face image capture processes that may be used in relation to user attached monitor device 110, and/or face image comparison processes that may be used to determine whether captured face image matches an expected face image in accordance with different embodiments.

Where the captured face image does not match the expected face image (block 725), a Mismatch condition is returned (block 730). Alternatively, where the captured face image matches the expected face image (block 725), a Match condition is returned (block 735). As discussed above in relation to FIG. 3 and FIG. 4, the respective Timeout condition, Mismatch condition, and Match condition dictate the generation of a tamper indication and corresponding tamper notification.

Figure 8:
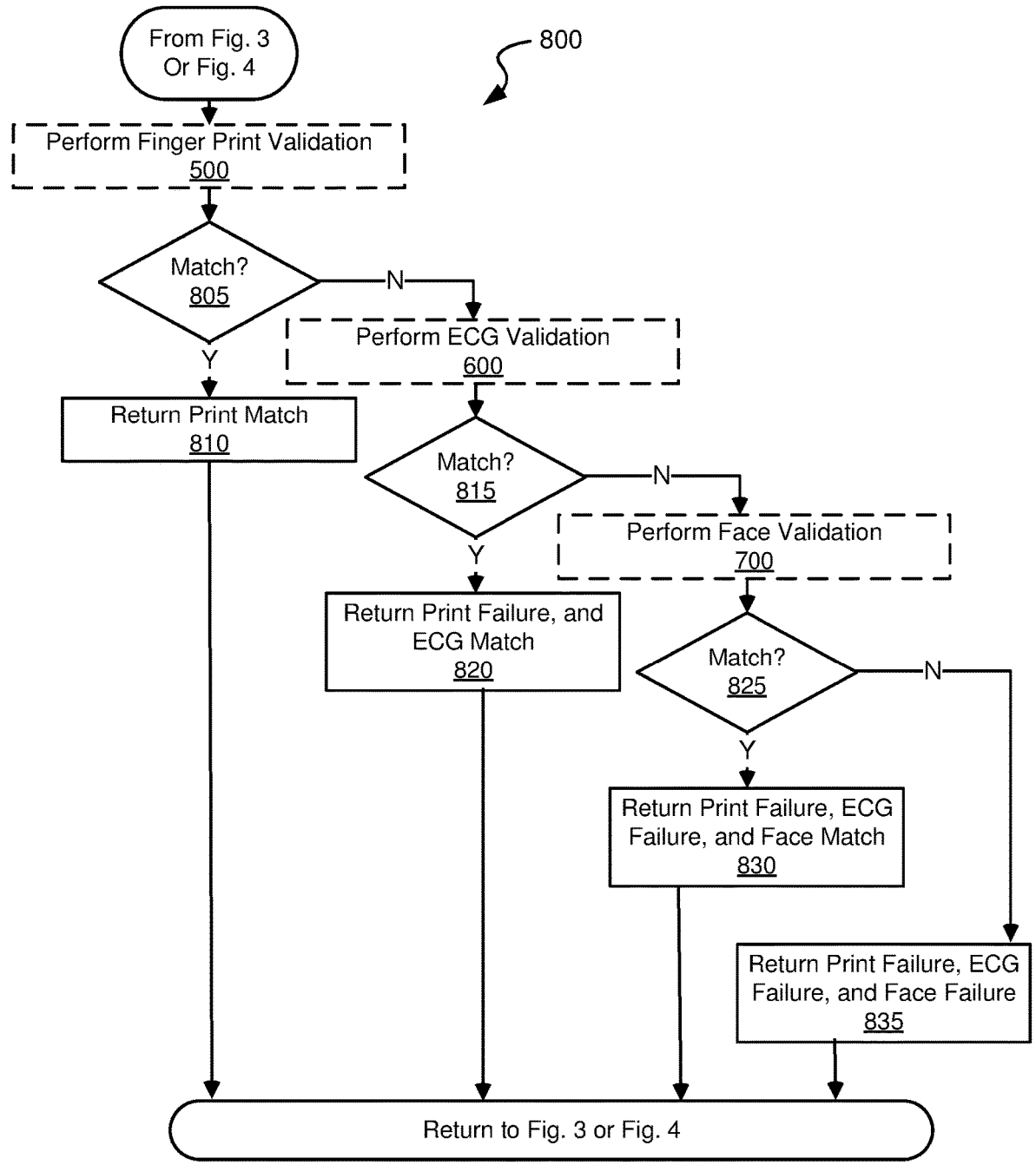
FIG. 8 is a flow diagram showing the tamper detection method of FIG. 3 or FIG. 4 tailored to use a combination of two or more sensed, active biometric data as part of secondary testing in accordance with some embodiments.

FIG. 8 is a flow diagram showing the tamper detection method of FIG. 3 or FIG. 4 tailored to use a combination of two or more sensed, active biometric data as part of secondary testing in accordance with some embodiments. Following flow diagram 500, the processes of previously discussed flow diagram 500 are performed for finger print validation (block 500). Block 500 is shown in dashed lines as it includes the processes discussed above in relation to FIG. 5. It is determined whether the finger print validation (block 500) yielded a matched finger print (block 805). Where a finger print is match is found within the timeout period (block 805), a Match condition is returned (block 810). As discussed above in relation to FIG. 3 and FIG. 4, the Match condition dictates the generation of a tamper indication and corresponding tamper notification.

Alternatively, where a finger print is match is not found within the timeout period (block 805), the processes of previously discussed flow diagram 600 are performed for ECG validation (block 600). Block 600 is shown in dashed lines as it includes the processes discussed above in relation to FIG. 6. It is determined whether the ECG validation (block 600) yielded a matched ECG (block 815). Where an ECG match is found within the timeout period (block 815), a Match condition is returned (block 820). As discussed above in relation to FIG. 3 and FIG. 4, the Match condition dictates the generation of a tamper indication and corresponding tamper notification.

Alternatively, where an ECG match is not found within the timeout period (block 815), the processes of previously discussed flow diagram 700 are performed for Face validation (block 700). Block 700 is shown in dashed lines as it includes the processes discussed above in relation to FIG. 7. It is determined whether the face validation (block 700) yielded a matched face image (block 825). Where a face image match is found within the timeout period (block 825), a Match condition is returned (block 830). As discussed above in relation to FIG. 3 and FIG. 4, the Match condition dictates the generation of a tamper indication and corresponding tamper notification. Where, on the other hand, a face image match is not found within the timeout period (block 825), a Mismatch condition is returned (block 830).

In conclusion, the present invention provides for novel systems, devices, and methods for monitoring individuals and/or assets. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A method for monitoring, the method comprising:
    providing a user attached monitor, wherein the user attached monitor device includes:
        a strap operable to secure the user attached monitor device to a wrist of a monitored individual;
        a first sensor for detecting a sensed, passive biometric data; and
        a second sensor for detecting a sensed, active biometric data;
        a continuity-based tamper sensor including a conductive element extending through the strap;
    receiving the sensed, passive biometric data;
    based at least in part upon the sensed, passive biometric data, requesting the monitored individual engage the user attached monitor device to enable the second sensor to sense the sensed, active biometric data;
    detecting a continuity status using the continuity-based tamper sensor; and
    determining a tamper status of the user attached monitor device based at least in part on a combination of the continuity status and at least one of the sensed, passive biometric data and the sensed, active biometric data.

2. The method of claim 1, wherein the first sensor is selected from a group consisting of: a pulse sensor; a blood oxygen sensory, a proximity sensor, a body temperature sensor, and a motion sensor.

3. The method of claim 1, the method further comprising:
    reporting the tamper status to a central monitor station via a wireless communication network.

4. The method of claim 1, wherein the sensed, passive biometric data is a pulse rate of the monitored individual.

5. The method of claim 1, wherein the sensed, active biometric data is selected from a group consisting of: a finger print of the monitored individual, a face image of the monitored individual, and an electrocardiogram of the monitored individual.

6. The method of claim 1, wherein the first sensor is a pulse sensor.

7. The method of claim 1, wherein the second sensor is selected from a group consisting of: a finger print sensor, an image sensor, and an electrocardiogram sensor.

8. The method of claim 1, wherein requesting the monitored individual engage the user attached monitor device includes alerting the monitored individual of a requested test via one or more of: a display on the user attached monitor device; a vibrator on the user attached monitor device; and a speaker on the user attached monitor device.

9. The method of claim 1, where requesting the monitored individual engage the user attached monitor device includes instructions provided via the display of the user attached monitor device guiding the monitored individual on how to engage the user attached monitor device to perform the requested test.

10. A monitoring system, the monitoring system comprising:
    a user attached monitor device including:
        a strap operable to secure the user attached monitor device to a wrist of a monitored individual;
        a first sensor for detecting a sensed, passive biometric data;
        a second sensor for detecting a sensed, active biometric data;
        a continuity-based tamper sensor including a conductive element extending through the strap;
        a processor; and
        a computer readable medium including non-transitory instructions executable by the processor to:
            receive the sensed, passive biometric data;
            based at least in part upon the sensed, passive biometric data, requesting the monitored individual engage the user attached monitor device to enable the second sensor to sense the sensed, active biometric data;
            detect a continuity status using the continuity-based tamper sensor; and
            determine a tamper status of the user attached monitor device based at least in part on a combination of the continuity status and at least one of the sensed, passive biometric data and the sensed, active biometric data.

11. The system of claim 10, wherein the first sensor is selected from a group consisting of: a pulse sensor; a blood oxygen sensory, a proximity sensor, a body temperature sensor, and a motion sensor.

12. The system of claim 10, the system further comprising:
    a central monitoring station; and
    wherein the non-transitory instructions are further executable to report the tamper status to a central monitoring station via a wireless communication network.

13. The system of claim 10, wherein the sensed, passive biometric data is a pulse rate of the monitored individual.

14. The system of claim 10, wherein the sensed, active biometric data is selected from a group consisting of: a finger print of the monitored individual, a face image of the monitored individual, and an electrocardiogram of the monitored individual.

15. The system of claim 10, wherein the first sensor is a pulse sensor.

16. The system of claim 10, wherein the second sensor is selected from a group consisting of: a finger print sensor, an image sensor, and an electrocardiogram sensor.

17. The system of claim 10, wherein requesting the monitored individual engage the user attached monitor device includes alerting the monitored individual of a requested test via one or more of: a display on the user attached monitor device; a vibrator on the user attached monitor device; and a speaker on the user attached monitor device.

18. The system of claim 10, where requesting the monitored individual engage the user attached monitor device includes instructions provided via the display of the user attached monitor device guiding the monitored individual on how to engage the user attached monitor device to perform the requested test.

19. A monitoring system, the monitoring system comprising:
- a user attached monitor device including:
  - a biometric sensor for detecting at least one of a sensed, passive biometric data or a sensed, active biometric data, and to provide a sensed biometric data;
  - a continuity-based tamper sensor including a conductive element extending through the strap;
  - a processor; and
  - a computer readable medium including non-transitory instructions executable by the processor to:
    - receive the sensed biometric data;
    - detect a continuity status using the continuity-based tamper sensor; and
    - determine a tamper status of the user attached monitor device based at least in part on a combination of the continuity status and the sensed biometric data and the sensed, active biometric data.

20. The monitoring system of claim 19, wherein the sensed biometric data is a sensed, passive biometric data.

21. The monitoring system of claim 19, wherein the sensed biometric data is a sensed, active biometric data.

22. The monitoring system of claim 19, wherein the sensed biometric data includes both a sensed, passive biometric data and a sensed, active biometric data.

23. The monitoring system of claim 19, wherein the biometric sensor includes an active biometric sensor selected from a group consisting of: a finger print sensor, an image sensor, and an electrocardiogram sensor.

24. The monitoring system of claim 19, wherein the user attached monitor device further includes a strap operable to secure the user attached monitor device to a wrist of a monitored individual.

25. The monitoring system of claim 19, wherein the biometric sensor includes a pulse sensor.

* * * * *